US008214756B2

(12) United States Patent
Salazar-Ferrer et al.

(10) Patent No.: US 8,214,756 B2
(45) Date of Patent: Jul. 3, 2012

(54) USER INTERFACE FOR ITERATIVE IMAGE MODIFICATION

(75) Inventors: Pascal Salazar-Ferrer, Eden Prairie, MN (US); Samuel Peterson, Santa Monica, CA (US)

(73) Assignee: Vital Images, Inc., Minnetonka, MN (US)

( * ) Notice: Subject to any disclaimer, the term of this patent is extended or adjusted under 35 U.S.C. 154(b) by 861 days.

(21) Appl. No.: 12/277,499

(22) Filed: Nov. 25, 2008

(65) Prior Publication Data
US 2010/0131887 A1    May 27, 2010

(51) Int. Cl.
*G06F 3/00* (2006.01)
*G06F 3/048* (2006.01)

(52) U.S. Cl. ........ 715/765; 715/757; 715/781; 715/810; 382/131; 128/922; 378/21; 378/37

(58) Field of Classification Search .................. 715/700, 715/764, 765, 781, 810, 961, 964, 968; 700/17, 700/65, 83, 84, 85, 98, 180, 182; 703/1; 705/3; 382/128, 131; 128/920, 922; 378/21, 378/37; 600/407

See application file for complete search history.

(56) References Cited

U.S. PATENT DOCUMENTS

| 5,803,914 | A  | * | 9/1998  | Ryals et al. .................... 600/407 |
| 6,219,059 | B1 |   | 4/2001  | Argiro |
| 6,484,048 | B1 | * | 11/2002 | Hoshino et al. ............... 600/410 |
| 6,720,966 | B2 | * | 4/2004  | Barth et al. .................... 345/424 |
| 2002/0106116 | A1 |   | 8/2002  | Knoplioch et al. |
| 2005/0122343 | A1 |   | 6/2005  | Bailey et al. |
| 2006/0280351 | A1 | * | 12/2006 | Luping et al. ................. 382/128 |
| 2007/0038085 | A1 | * | 2/2007  | Zhang et al. .................. 600/437 |
| 2007/0116357 | A1 | * | 5/2007  | Dewaele ....................... 382/173 |
| 2008/0155451 | A1 | * | 6/2008  | Lundstrom et al. ........... 715/772 |
| 2010/0086185 | A1 | * | 4/2010  | Weiss ............................ 382/131 |

FOREIGN PATENT DOCUMENTS
WO    2008052226 A2    5/2008

OTHER PUBLICATIONS

Blake, A. et al., "Interactive Image Segmentation using an adaptive GMMRF model", Microsoft Research Cambridge UK, 7 JJ Thomson Avenue, Cambridge CB3 0FB, UK, pp. 1-14.

Wang, Chao et al., "Progressive Cut", University of Science and Technology of China, Hefei; Microsoft Research Asia; Tsinghua University; 10 pages.

International Search Report and Written Opinion Issued in PCT/US2009/065873, mailed Jan. 21, 2010, 11 pages.

(Continued)

*Primary Examiner* — Xiomar L Bautista
(74) *Attorney, Agent, or Firm* — Faegre Baker Daniels LLP

(57) ABSTRACT

A user interface for display or editing of a three dimensional medical image is provided on a display and is responsive to user inputs in a medical imaging system. The user interface includes a framing tool for defining a region of interest on the medical image. An image matrix is then provided on the user interface, which includes a plurality of cross-sectional images each corresponding to a cross-section of the medical image at one of a plurality of cut planes within the region of interest. One or more reference views of the medical image are also displayed, which each include a plurality of reference indicia, each of which corresponds to a location of one of the plurality of cut planes.

21 Claims, 10 Drawing Sheets

OTHER PUBLICATIONS

Blake, A. et al., "Interactive Image Segmentation using an adaptive GMMF model", Microsoft Research Cambridge UK, 7 JJ Thomson Avenue, Cambridge CB3 0FB, UK, pp. 1-14.

Li, Yin et al., "Lazy Snapping", Hong Kong University of Science and Technology, pp. 303-308.

Luo, Huitao et al., "Designing an Interactive Tool for Video Object Segmentation and Annotation", Advent Group, Columbia University, 12 pages.

Mortensen, Eric N. et al., "Intelligent Scissors for Image Composition", Brigham Young University, 8 pages.

Neufeld, Eric et al., "Mixed initiative Interactive Edge Detection", Department of Computer Science, University of Saskatchewan, 8 pages.

Rother, Carsten et al., "GrabCut—Interactive Foreground Extraction Using Iterated Graph Cuts", Microsoft Research Cambridge, UK, 6 pages.

Vezhnevets, Vladimir et al., ""GrowCut"—Interactive Multi-Label N-D Image Segmentation by Cellular Automata", Graphics and Media Laboratory, Faculty of Computational Mathematics and Cybernetics, Moscow State University, Moscow, Russia, 7 pages.

Wang, Chao et al., "Progressive Cut", University of Science and Technology of China, Hefei; Microsoft Research Asia; Tsinghua University; 10 pages, Oct. 23, 2006.

* cited by examiner

USER INTERFACE FOR ITERATIVE IMAGE MODIFICATION

TECHNICAL FIELD

The present invention relates to graphical user interfaces for imaging applications. More particularly, the present invention relates to a graphical user interface for iterative medical image segmentation and editing.

BACKGROUND

Due to the increasingly fast processing power of modem-day computers, users have turned to computers to assist them in the examination and analysis of images of real-world data. For example, within the medical community, medical professionals who once examined x-rays hung on a light screen now use computers to examine images obtained via ultrasound, computed tomography (CT), magnetic resonance (MR), ultrasonography, positron emission tomography (PET), single photon emission computed tomography (SPECT), magnetic source imaging, and other imaging techniques.

Each of the above-identified imaging procedures generates volume images, although each relies on a different technology to do so. For example, CT uses an x-ray source to rapidly rotate around a patient to obtain up to hundreds of electronically stored pictures of the patient. On the other hand, MR uses radio-frequency waves that are emitted to cause hydrogen atoms in the body's water to move and release energy, which is then detected and translated into an image. Because each of these techniques penetrates the body of a patient to obtain data, and because the body is three-dimensional, this data represents a three-dimensional image, or volume. In particular, CT and MR both provide three-dimensional (3D) "slices" of the body, which can later be electronically reassembled.

An important aspect in the use of medical images for diagnosing physiological conditions is the accurate segmentation of the region of interest in the image to identify the boundaries of the region and other anatomical structures. For example, assignment of the appropriate therapy or dose to treat a physiological condition may necessitate the volume being accurately measured. In 3D medical images, both boundary-based segmentation methods and region-based segmentation methods may be used to assist in the segmentation of organs, pathologies, vessel contours, or other volumes of interest. In boundary-based segmentation methods, the boundaries of the volume of interest are outlined by the user with an on-screen tool. In region-based segmentation methods, the user establishes seed points as examples of the regions to include in or exclude from the segmented image. However, in both methods, the user has a limited visibility of the volume of interest to segment or to edit, and the process of defining the boundaries of the volume of interest in three dimensions can be a very time consuming process.

SUMMARY

The present invention relates to a user interface for iterative segmentation and editing of a three dimensional image. The user interface is provided on a display and is responsive to user inputs in an imaging system. The user interface includes a framing tool for defining a region of interest on the medical image. An image matrix is then provided on the user interface, which includes a plurality of cross-sectional images each corresponding to a cross-section of the medical image at one of a plurality of cut planes within the region of interest. One or more reference views of the medical image are also displayed, which each include a plurality of reference indicia, each of which corresponds to a location of one of the plurality of cut planes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
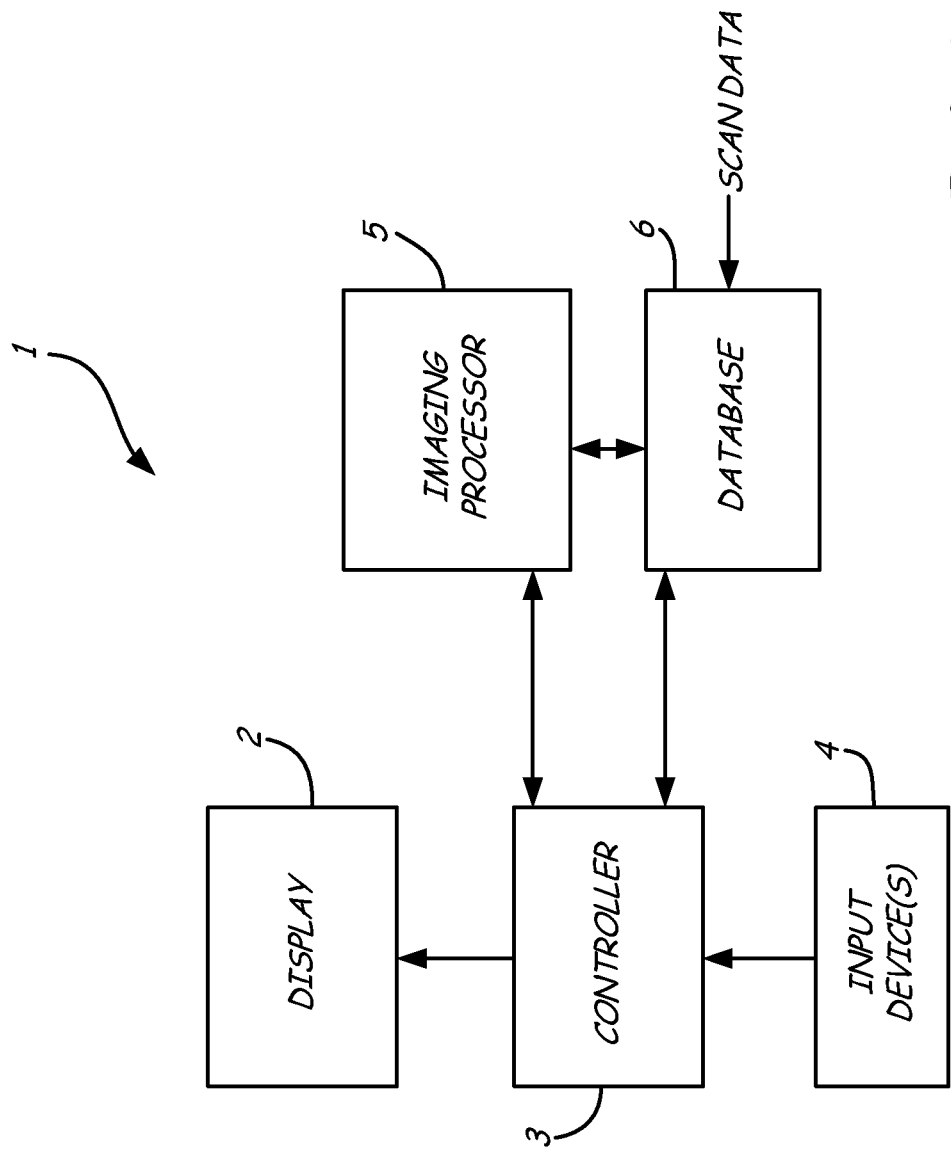
FIG. 1 is a block diagram of an embodiment of a medical imaging system that employs the user interface according to the present invention.

FIG. 1 is a block diagram of a medical imaging system 1 including a display 2, a controller 3, one or more input devices 4, an imaging processor 5, and an image database 6. The controller 3 receives inputs from the one or more input devices 4 and provides an output to the display 2. The display 2, the controller 3, and the one or more input devices 4 may be configured as a computer workstation, and the one or more input devices 4 may include, for example, a mouse, keyboard, or digital interactive pen. The controller 3 communicates with and controls both the imaging processor 5 and the image database 6. In some embodiments, the imaging processor 5 and the image database 6 are located locally with the controller 3. In other embodiments, the controller 3 communicates with and controls the imaging processor 5 and the image database 6 through the internet, such as via a web-based application run on the controller 3.

The image database 6 receives and stores raw data from one or more scans (e.g., CT or MR scan) of a patient. The data from the one or more scans may be used by the imaging processor 5 to assemble the scans into a three dimensional (3D) image of the anatomical feature being analyzed. One example method for assembling scans into a 3D medical image that may be employed by the imaging processor 5 is described in U.S. Pat. No. 6,219,059, entitled "Interactive Control of Voxel Attributes Using Selectable Characteristics," which is hereby incorporated by reference in its entirety. The imaging processor 5 may also isolate an anatomical feature of interest from the surrounding anatomy based on the response of each portion of the anatomy to the scan. For example, the anatomical feature of interest may have a different density (i.e., a different level of transparency to the scan signal) than the surrounding anatomy, and the different portions of the anatomy can thus be separated by the imaging processor 5 from each other based on this varying level of density. The imaging processor 5 may then store data related to the assembled 3D medical image in the imaging database 6.

Figure 2:
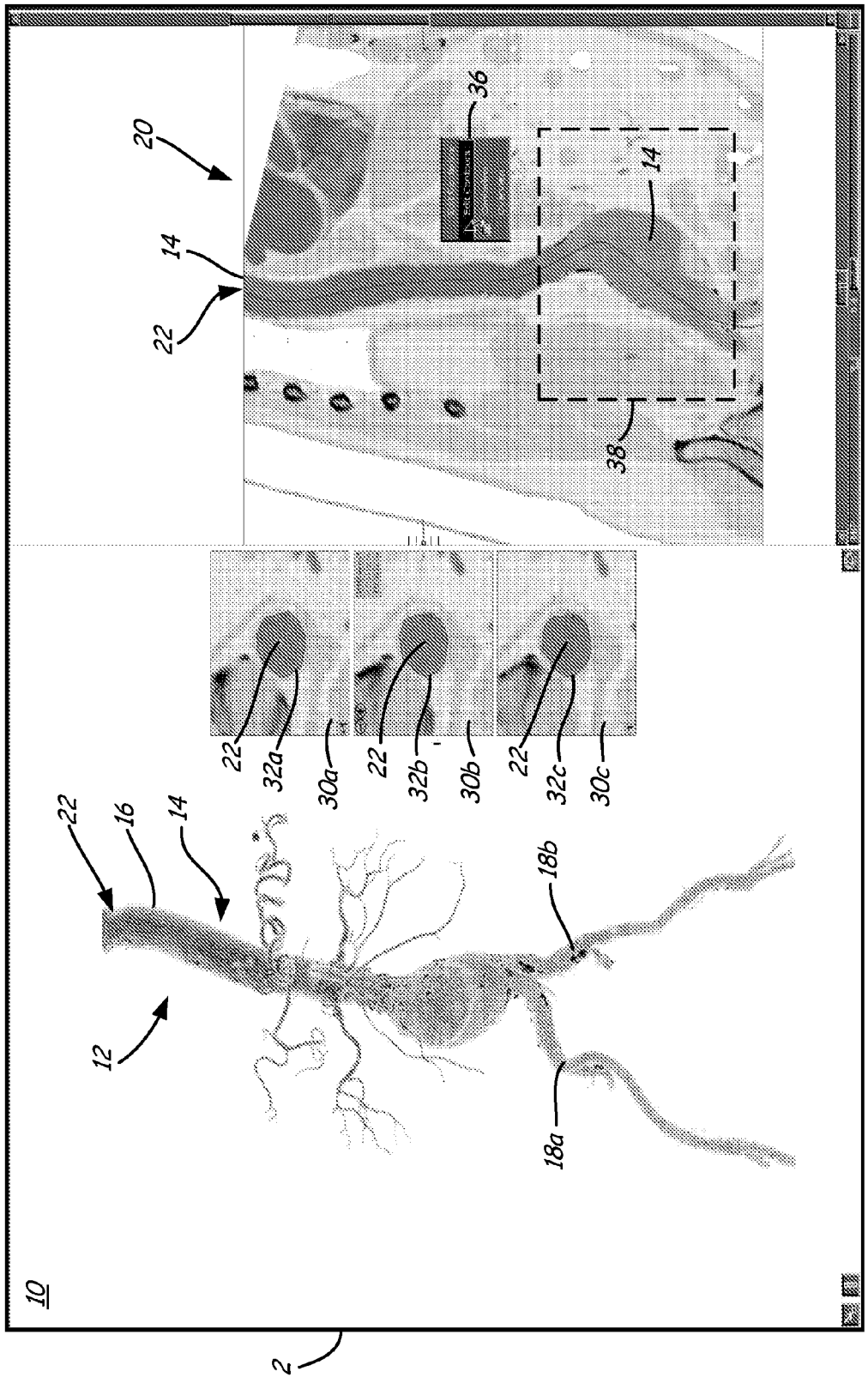
FIG. 2 is a screen shot of a user interface for a medical imaging system according to the present invention showing a three dimensional image of a vessel and a cross-sectional view of the vessel.

FIG. 2 is a screen shot of a user interface 10 for use in a medical imaging system (e.g., medical imaging system 1) according to the present invention. The user interface 10 is provided on the display 2 in the medical imaging system 1 to allow a user to display and iteratively segment and/or edit a medical image generated from one or more scans (e.g., CT or MR scan) of a patient. The user may interact with the user interface 10 using any of the one or more input devices 4 connected to the medical imaging system 1.

In the embodiment shown in FIG. 2, a 3D image 12 of an aorta 14 is provided in the left side of the user interface 10. The aorta 14 imaged in FIG. 2 shows the trunk 16 and iliacs 18a and 18b. The user interface 10 also includes a curved planar reformatted image 20 of the trunk 16 taken along the longitudinal dimension of the aorta 14. The aorta 14 is shown with surrounding portions of the patient's anatomy in the curved planar reformatted image 20, which is provided on the right side of the user interface 10 in the embodiment shown. The 3D image 12 and the curved planar reformatted image 20 each include a centerline 22, which is an imaginary line traversing the center of the aorta 14. The centerline 22 may be estimated by the medical imaging system 1 based on information from the scans of the aorta 14, as is known in the art.

FIG. 2 also shows optional axial cross-sectional images 30a, 30b, and 30c, which are each cross-sections of the aorta 14 in a plane perpendicular to the centerline 22 at a point of intersection between the plane and the centerline 22. The axial cross-sectional images 30a-30c depict cross-sectional views taken at different locations along the length of the trunk 16 of the aorta 14 in a plane perpendicular to the centerline 22. The axial cross-sectional images 30a, 30b, and 30c include the outer contours 32a, 32b, and 32c, respectively, of the aorta 14 at the locations of the axial cross-sectional images 30a-30c. Similar to the centerline 22, the outer contours 32a, 32b, and 32c may be estimated by the medical imaging system 1 based on information from the scans of the aorta 14, or by using tools in the user interface 10 to set and edit the outer contours 32a, 32b, and 32c, as will be described in more detail below. The axial cross-sectional images 30a-30c also show the position of the centerline 22 with respect to the contours 32a-32c.

The user interface 10 according to the present invention allows a user of the medical imaging system 1 to define the region of interest in the analyzed anatomical feature to view, segment, and/or edit. In the embodiment shown in FIG. 2, the user may initiate a menu 36 with an appropriate input with the one or more input devices 4 to the medical imaging system 1 (e.g., by right-clicking a mouse). The menu 36 provides options for modifying or controlling aspects of the 3D image 12, the curved planar reformatted image 20, and/or the axial cross-sectional images 30a-30c. For example, the menu 36 shown includes options to "Edit Centerline," which initiates one or more tools for the user to modify the location of the centerline 22, "Edit Contours," which initiates one or more tools for the user to modify the contours of the (e.g., contours 32a-32c) aorta 14 along the length of the aorta 14, "Centerline," which toggles whether the centerline 22 is shown in the 3D image 12 and the curved planar reformatted image 20, and "Overview," which provides tools related to conducting measurements of elements of the medical image.

As discussed above, an important aspect in the use of medical images for diagnosing physiological conditions is the accurate segmentation of the region of interest in the image to identify the boundaries of the region and other anatomical structures. The user interface 10 according to the present invention allows the user to precisely define the contours of an anatomical feature by providing tools to iteratively manipulate the mapped boundaries of the anatomical feature. To begin this process in the user interface 10, the user selects the "Edit Contours" option on the menu 36. In some embodiments, selecting the "Edit Contours" option enables a framing tool to allow the user to select a region of interest on the anatomical feature (in this case, the aorta 14) to concentrate the segmentation and contouring to select ranges of the volume. The framing tool may allow the user to draw a box 38 around the region of interest, as shown in FIG. 2. This reduces the processing time of the editing process, since the medical imaging system 1 only needs to process changes for a smaller portion of the overall medical image. Alternatively, the selection of the "Edit Contours" option on the menu 36 may initiate a boundary editing tool without initiating a framing tool, especially if the curved planar reformatted image 20 includes a satisfactorily small segment of the anatomy for segmentation and contouring.

Figure 3:
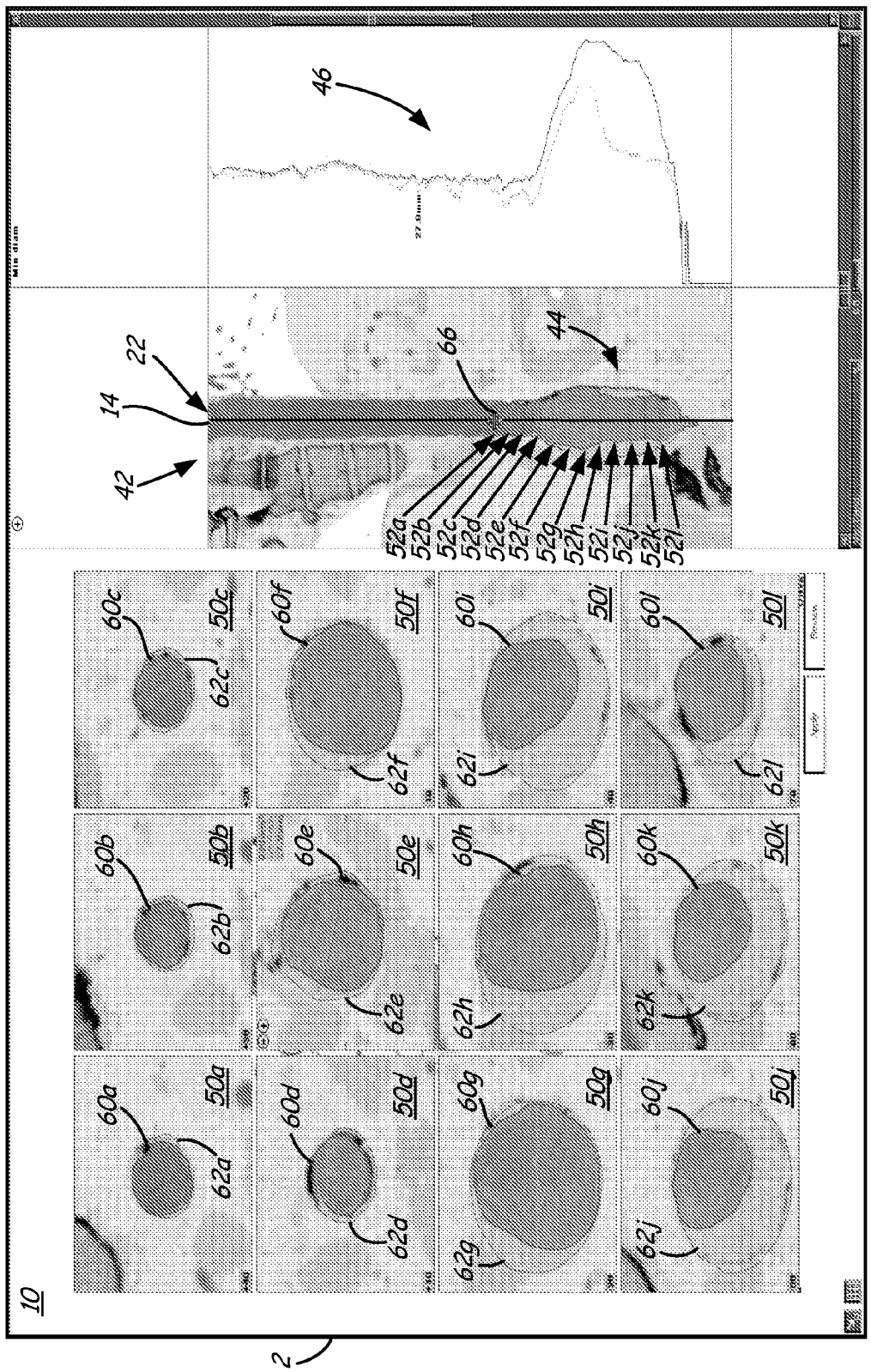
FIG. 3 is a screen shot of the user interface after a region of interest in the vessel is selected, showing a matrix of cross-sectional images and a cross section of the region of interest including reference indicia.

FIG. 3 is a screen shot of the user interface 10 after a region of interest in the aorta 14 is selected using the framing tool in FIG. 2. The user interface 10 includes a matrix 40 of cross-sectional images, a straightened curved planar reformatted cross-sectional image 42 including the region of interest 44, and a graph 46 of the inner and outer diameters of the aorta 14. In the embodiment shown, the matrix 40 is a three-by-four matrix of images including cross-sectional images 50a, 50b, 50c, 50d, 50e, 50f, 50g, 50h, 50i, 50j, 50k, and 50l. The cross-sectional image 42 includes a plurality of reference indicia (e.g., lines) 52a, 52b, 52c, 52d, 52e, 52f, 52g, 52h, 52i, 52j, 52k, and 52l substantially perpendicular to the centerline 22. It will be appreciated that the reference indicia may have other forms. The reference indicia 52a-52l represent the locations of cut planes through the aorta 14 that provide the cross-sections shown in respective cross-sectional images 50a-50l. In some embodiments, the medical imaging system 1 modifies the contours of the cross-sectional image 42 of the aorta 14 when the region of interest 44 is selected such that the centerline 22 is straight in the straightened curved planar reformatted cross-sectional image 42. Consequently, the reference indicia 52a-52l are substantially parallel with respect to each other along the region of interest 44. In the embodiment shown, the reference indicia 52a-52l are spaced apart at substantially distance with respect to each other, with an overall distance between indicia 52a and 52l of 110 mm. Thus, the matrix 40 illustrates cross-sections of the aorta 14 at 10 mm increments along the region of interest 44. It will be appreciated that the distance between reference indicia 52a-52l may be defined by the user, and that the reference indicia 52a-52l may be regularly or irregularly spaced with respect to each other.

In one alternative embodiment, the aorta 14 is displayed unmodified in the straightened curved planar reformatted cross-sectional image 42, with the centerline 22 following the center of the aorta 14 and the reference indicia 52*a*-52*l* being arranged perpendicular to the centerline 22. In another alternative embodiment, the reference indicia 52*a*-52*l* are oriented relative to something other than the centerline 22 (e.g., the long axis of the body).

While twelve reference indicia 52 and twelve corresponding cross-sectional images 50 are shown, it will be appreciated that the user interface 10 may be adapted to provide any number of reference indicia 52 for an equivalent number of cross-sectional images 50 in the matrix 40. For example, the user interface 10 may be configured to allow the user to increase or decrease the number of reference indicia 52 in the cross-sectional image. This option may be provided to the user through a menu on the user interface 10, similar to menu 36 in FIG. 2. The matrix 40 may be adapted to provide an appropriate number of cross-sectional images based on the number of reference indicia 52. The cross-sectional images in the matrix 40 may also be arranged based on the configuration of the display 2. For example, if the display has a widescreen aspect ratio (e.g., 16:9), then the matrix 40 may display more cross-sectional images in the rows of the matrix 40.

Each cross sectional image 50*a*-50*l* includes an inner contour 60*a*-60*l*, respectively, and an outer contour 62*a*-62*l*, respectively. For example, cross-sectional image 50*j* includes an inner contour 60*j* and an outer contour 62*j*. In each cross-sectional image 50*a*-50*l*, the inner contour 60*a*-60*l* represents the area through which blood flows in the aorta 14, and the outer contour 62*a*-62*l* represents the outer wall of the aorta 14. Thus, as will be described, the user interface 10 may be used to measure the precise dimensions of a thrombus or other blockage that is preventing blood from flowing completely though the aorta 14. While two contours are shown, it will be appreciated that the user interface 10 may be configured to allow the user to generate one or more than two contours on the anatomical feature being analyzed.

The user interface 10 also includes a selector tool 66 provided on the cross-sectional view 42. The selector tool 66 may be used to modify the distance between the reference indicia 52*a*-52*l* (individually or collectively), to modify the size of the region of interest 44 (i.e., to change the distance between reference indicia 52*a* and 52*l*), and/or to shift all reference indicia 52*a*-52*l* relative to the centerline 22 (not shown in FIG. 3) without affecting the spacing between the reference indicia 52*a*-52*l*. The selector tool 66 may be constantly available for use on the cross-sectional view 42, or it may be initiated through a menu similar to menu 36 described in FIG. 2. When the selector tool 66 is used to modify the arrangement of the reference indicia 52*a*-52*l*, the cross-sectional images 50*a*-50*l* are correspondingly modified to represent the new locations of the reference indicia 52*a*-52*l*, respectively. The cross-sectional images 50*a*-50*l* for the location of each reference indicia 52*a*-52*l* may be retrieved from images stored in the imaging database 6, or may be assembled by the imaging processor 5 from the raw scan data stored in the database 6. This allows the user to focus the cross-sectional images 50*a*-50*l* in the matrix 40 to the precise region of interest 44 the user wishes to edit, segment, and analyze.

Figure 4:
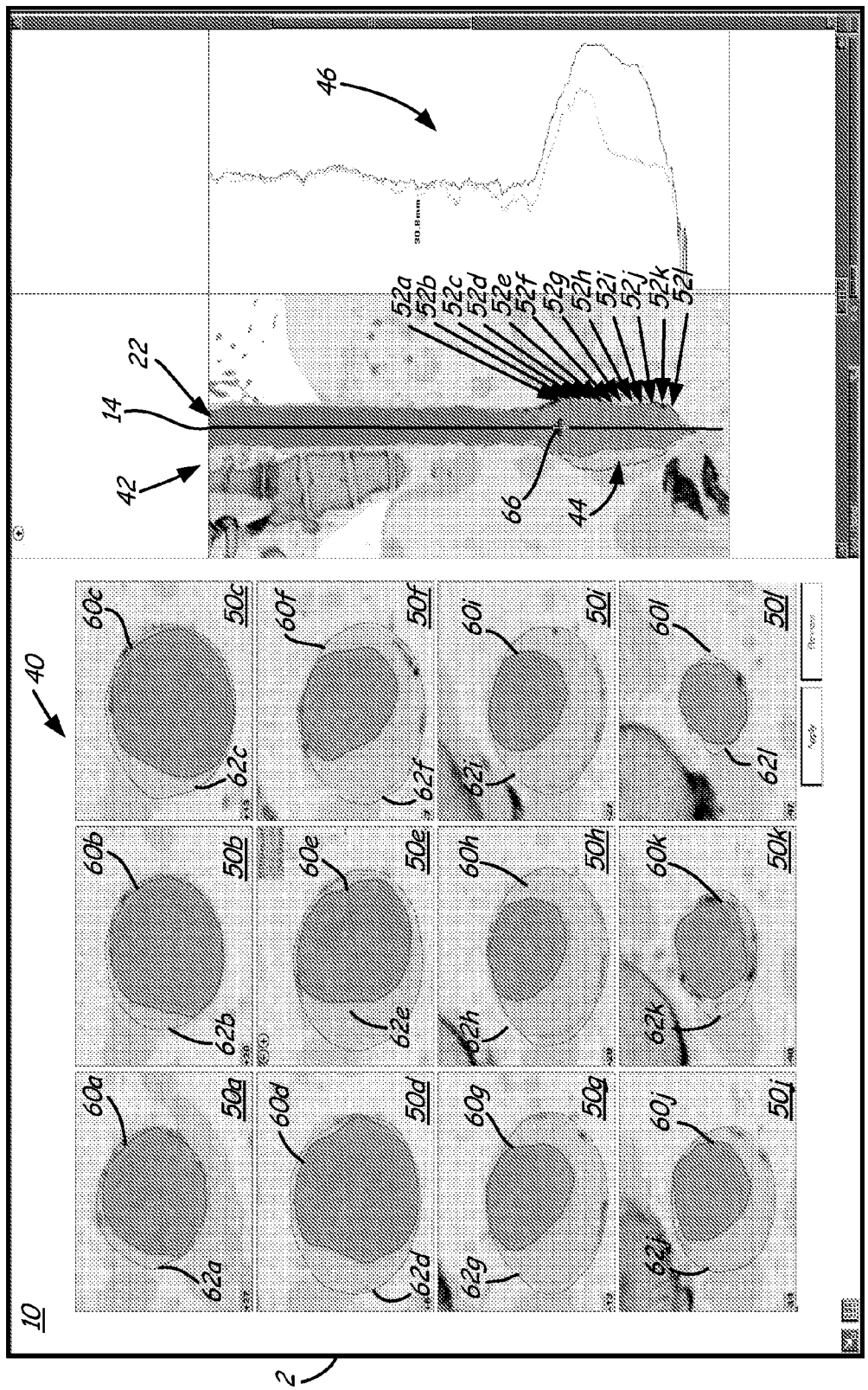
FIG. 4 is a screen shot of the user interface showing a selector tool for moving the reference indicia relative to the medical image.

To illustrate, FIG. 4 shows the effect of reducing the distance between each reference indicia 52*a*-52*l* by using the selector tool 66 to reduce the distance between reference indicia 52*a* and 52*l*. This reduces the distance across the cross-sectional images 50*a*-50*l*, allowing a more precise contour or editing region by reducing the overall selection length.

The modification of the distance between reference indicia 52*a*-52*l* may be accomplished by positioning the selector tool 66 over the reference indicium 52*a* and clicking the mouse, and subsequently dragging the reference indicium 52*a* to the new position. As illustrated, the reference indicia 52*a*-52*k* are moved collectively when the reference indicium 52*a* is selected, while reference indicium 52*l* remains at the same location, such that the spacing between reference indicia 52*a*-52*l* changes by a substantially uniform amount as reference indicium 52*a* is dragged. In the embodiment shown, the reference indicia 52*a*-52*l* are spaced apart by about 6-7 mm with respect to adjacent reference indicia, with an overall distance between lines 52*a* and 52*l* of 74 mm. The user interface 10 may alternatively provide the option to move only the selected reference indicium 52 without affecting the position of the other reference indicia. In addition, the selector tool 66 may alternatively be used to increase the overall distance between reference indicia 52*a*-52*l* to allow for faster contour and region editing.

Figure 5:
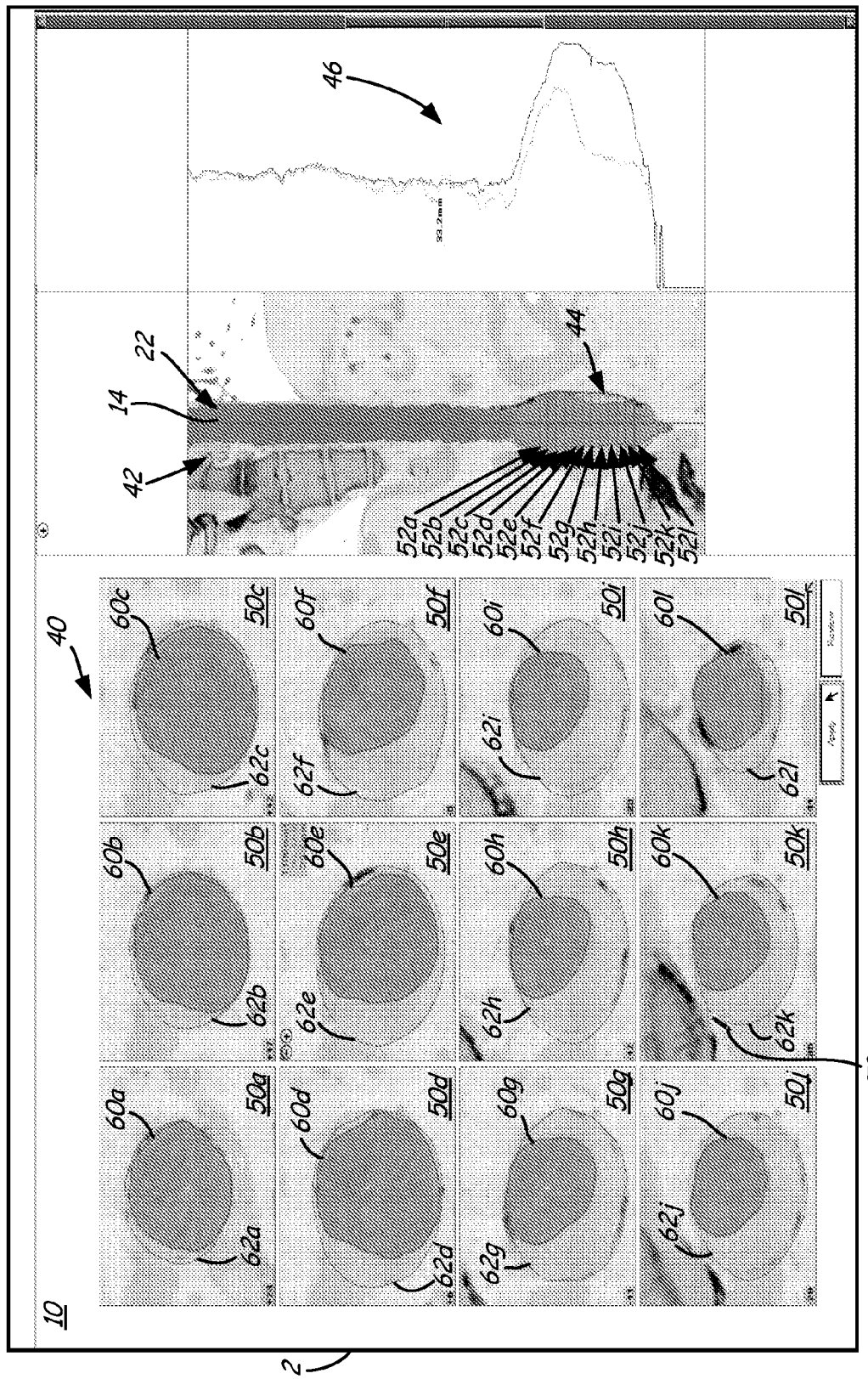
FIG. 5 is a screen shot of the user interface showing a boundary tool for defining the contours of the vessel on one of the cross-sectional images.

As discussed above, the user interface 10 may also provide the option to shift all reference indicia 52*a*-52*l* relative to the region of interest 44. FIG. 5 illustrates the result of shifting the reference indicia 52*a*-52*l* from the positions illustrated in FIG. 4 upwardly in the region of interest 44. As the reference indicia 52*a*-52*l* are shifted, the cross-sectional views 50*a*-50*l* correspondingly adjust to represent the cross-sectional views provided by cut planes at the locations of respective reference indicia 52*a*-52*l*.

In order to improve the accuracy of the inner contours 60 and the outer contours 62, the user interface 10 provides a boundary tool for adjusting the contour locations. The boundary tool may be selected as an option and initiated through a menu similar to menu 36. Alternatively, the boundary tool may be initiated with a toolbar (not shown) or through an input from the one or more input devices 4 (e.g., a keyboard, mouse, or digital interactive pen) to the medical imaging system 1. The boundary tool is shown as a stylus 70 in cross-sectional image 50*k* in FIG. 5. The stylus 70 may be used to draw around the boundaries of any of the inner contours 60*a*-60*l* and the outer contours 62*a*-62*l*. In addition, the stylus 70 may be used to draw around the boundaries of the aorta 14 in longitudinal cross-sectional image 42. In some embodiments, the contours are adjusted by freehand drawing around the boundaries of the inner contours 60 and the outer contours 62. Alternatively, the stylus may be configured to grab and drag portions of the inner contours 60 and outer contours 62 to modify the positioning of the boundaries.

When the inner contours 60 and the outer contours 62 in the cross-sectional views 50 have been modified, the user may actuate the "Apply" button 72 (e.g., by clicking on the button 72 with a mouse cursor). The "Apply" button initiates a program in the medical imaging system 1 that interpolates the inner and outer contours of the aorta 14 between the reference indicia 52*a*-52*l* based on the adjustments made to the inner contours 60 and the outer contours 62 using the boundary tool. That is, the medical imaging system 1 estimates the location of the inner and outer walls of the aorta 14 in the unedited portions of the contour based on the contour edits performed with the boundary tool. The medical imaging system 1 may include, as part of its interpolation algorithm, the constraint that the inner contours 60 remains within the outer contour 62 along the length of the aorta 14. The interpolation allows the user to accurately map the contours of the aorta 14 in the region of interest 44 without having to manually edit the contours along the entire region of interest 44.

Figure 6:
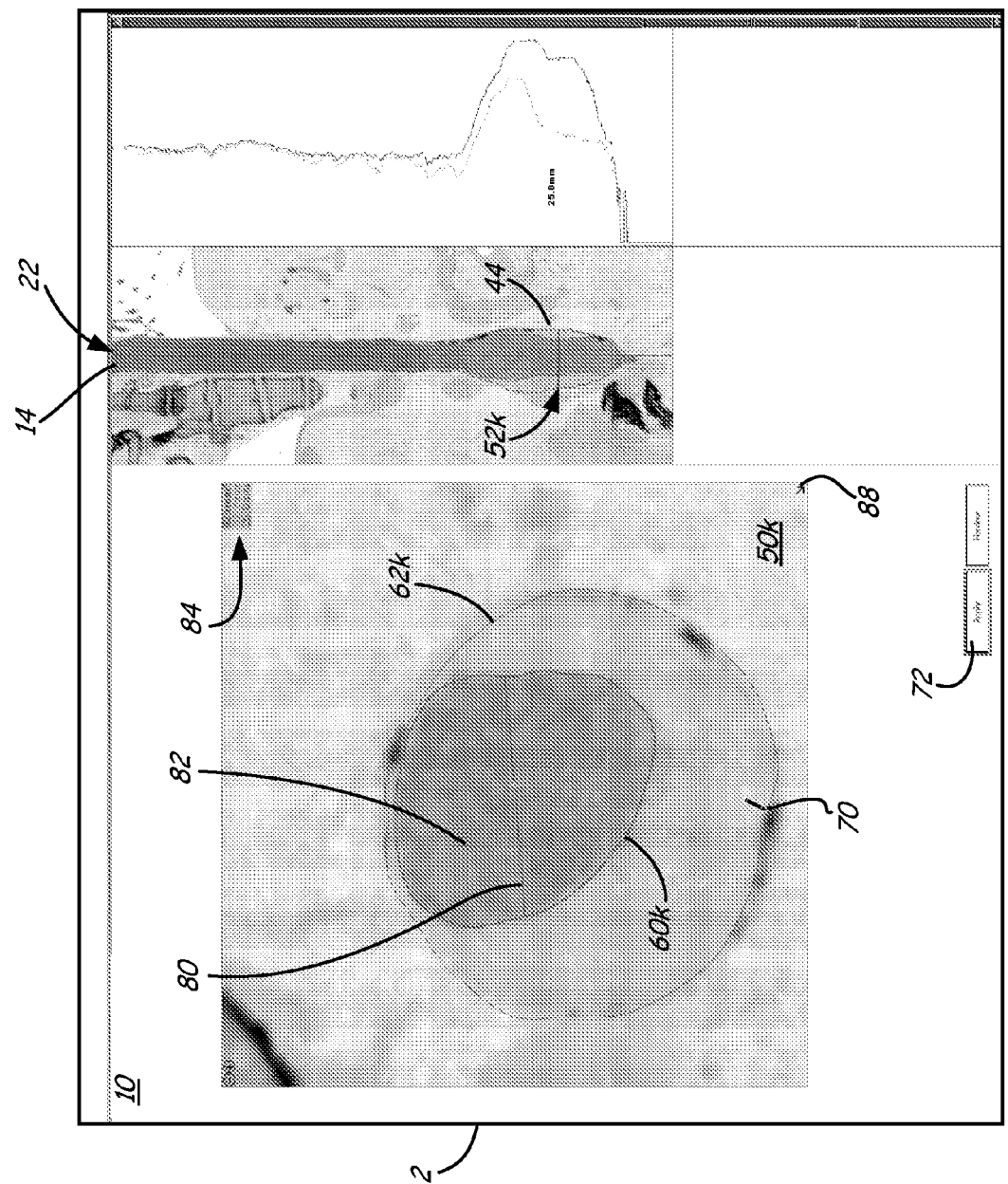
FIG. 6 is a screen shot of the user interface showing an enlarged cross-section from the matrix of cross-sectional images for contour editing.

If a higher resolution is desired to edit the inner contours 60 and/or the outer contours 62, the user interface 10 allows the user to select and enlarge one of the cross-sectional views 50 in the matrix 40. For example, FIG. 6 is a screen shot of the user interface 10 showing the cross-sectional view 50k from the matrix 40 in FIG. 5 after enlarging. In some embodiments, an interface is provided on each of the cross-sectional views 50 to select one of the cross-sectional views 50 for enlarging. In other embodiments, a menu is provided to select the cross-sectional view 50 to enlarge from the matrix 40. In FIG. 6, the enlarged cross-sectional view 50k allows the contours to be edited at a higher resolution, providing a means for more intricate editing of the inner contour 60k and the outer contour 62k with the stylus 70. The stylus 70 may be used, for example, to freehand draw the inner contour 60k and/or the outer contour 62k, or to grab and drag the contours 60k and 62k to adjust them to the appropriate position. When the contours 60k and 62k have been modified, the "Apply" button 72 may be actuated as described above to apply the changes to the region of interest 44, and to interpolate the dimensions of the aorta 14 in the adjacent regions based on the changes to the contours 60k and 62k.

After defining the inner contour 60k and the outer contour 62k, it may be desirable to measure the dimensions of the inner contour 60k and/or the outer contour 62k. The measurements may be used to diagnose a condition or to prescribe a course of therapy to treat a physiological condition, for example. The user interface 10 includes a measurement tool to measure the dimensions of the aorta. Access to the measurement tool may be provided through a menu similar to the menu 36 described above, or through another means on the user interface 10. In the embodiment shown in FIG. 6, the measurement tool provides a first line 80 showing the shortest distance across the inner contour 60k, and a second line 82 showing the longest distance across the inner contour 60k. These lines may be generated automatically by the measurement tool, or may be manually applied by the user. The lengths of the lines 80 and 82 may be provided in a dimensions box 84 on the cross-sectional image 50k. In the embodiment shown, the length of the first line 80 is 25.8 mm and the length of the second line 82 is 32.2 mm. The dimensions box 84 also shows the area within the inner contour 60k which, in the embodiment shown, is 625 mm². The dimensions of the outer contour 62k may similarly be determined using the measurement tool. It should be noted that while the measurement tool has been described as being used in the enlarged cross-sectional view mode shown in FIG. 6, the measurement tool may also be used when the user interface 10 provides the cross-sectional images in the matrix 40. When finished editing and measuring the cross-sectional image 50k, the user may actuate zoom tool 88 to return the user interface 10 to the screen including the matrix 40.

Figure 7:
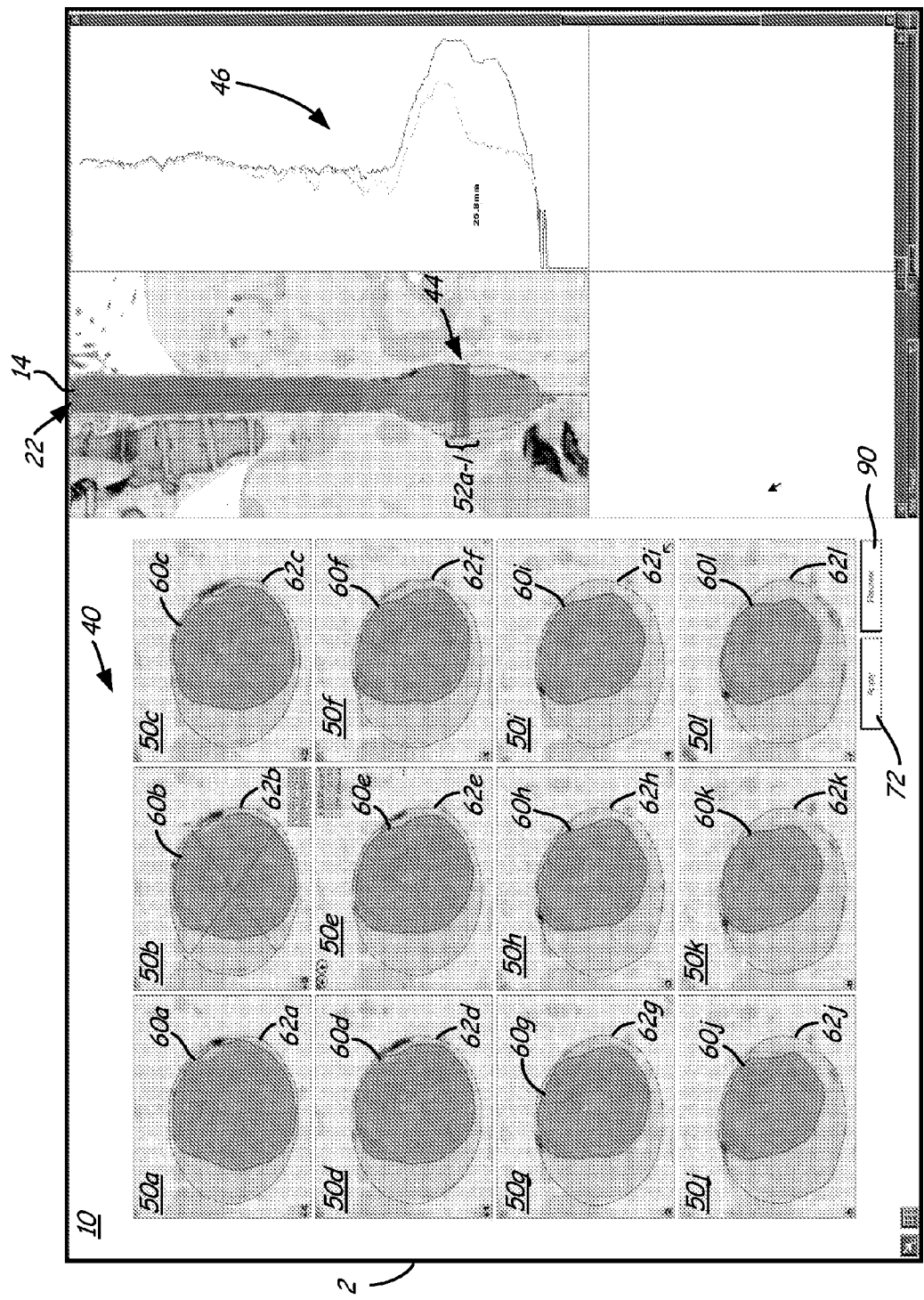
FIG. 7 is a screen shot of the user interface showing the matrix of cross-sectional images in review mode.

FIG. 7 is a screen shot of the user interface 10 in a review mode. The review mode is initiated on the user interface 10 by actuating the "Review" button 90 (e.g., by clicking on the button 90 with a mouse cursor). The review mode causes the reference indicia 52 to move closely together and to provide cross-sectional views 50 in the matrix 40 illustrating the views at the cut planes represented by the reference indicia 52. The review mode allows a user to review the interpolated contours 60 and 62 of the aorta 14 for accuracy, and to make any modifications to the contours in the reviewed cross-sectional views 50. In the embodiment shown, the reference indicia 52 are spaced about 1 mm from each other. The selector tool described above may be employed on the user interface 10 to translate the reference indicia 52 to other portions of the region of interest 44 to review the contours 60 and 62 for accuracy.

Figure 8:
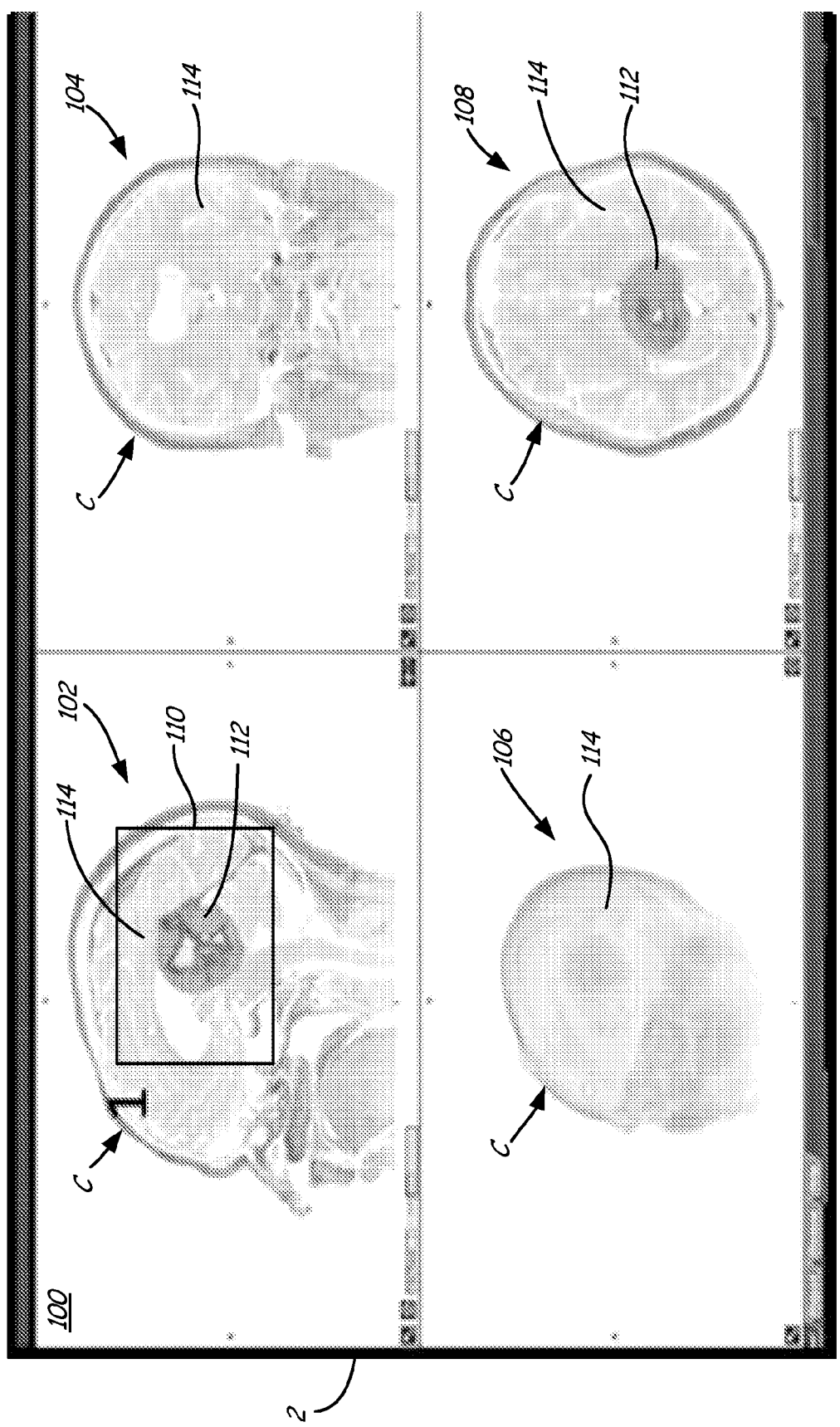
FIG. 8 is a screen shot of a user interface for a medical imaging system according to another embodiment of the present invention showing different views of a cranial image.

While the user interface 10 has been described with regard to editing and segmenting an aorta 14, it will be appreciated that other anatomical features may be imaged, segmented, and contoured, and the user interface may have other forms, features, and tools. For example, FIG. 8 is a screen shot of a user interface 100 for a medical imaging system 1 according to another embodiment of the present invention. The user interface 100 includes various cross-sectional views of a cranium C that are assembled from one or more scans (e.g., CT or MR scan) in a similar manner as described above with regard to FIG. 2. In particular, the user interface 100 includes a sagittal cross-sectional image 102, a coronal cross-sectional image 104, an oblique cross-sectional or 3D image 106, and an axial cross sectional image 108.

The user interface 100 according to the present invention also allows the user to define the region of interest in the analyzed anatomical feature to segment and/or edit. In the embodiment shown in FIG. 8, the user initiates a framing tool to draw a frame 110 around the region of interest of the cranium to be analyzed. The framing tool may be initiated through a menu similar to menu 36 described above, or with a button or other interface provided on the user interface 100. The frame 110 may be drawn around any portion of the cranium C on any of the cross-sectional image 102, 104, 106, and 108. In FIG. 8, the frame 110 is drawn around a tumor 112 in a brain 114. The user may adjust the size and location of the frame 110 to modify the positioning of the selected region of interest.

Figure 9:
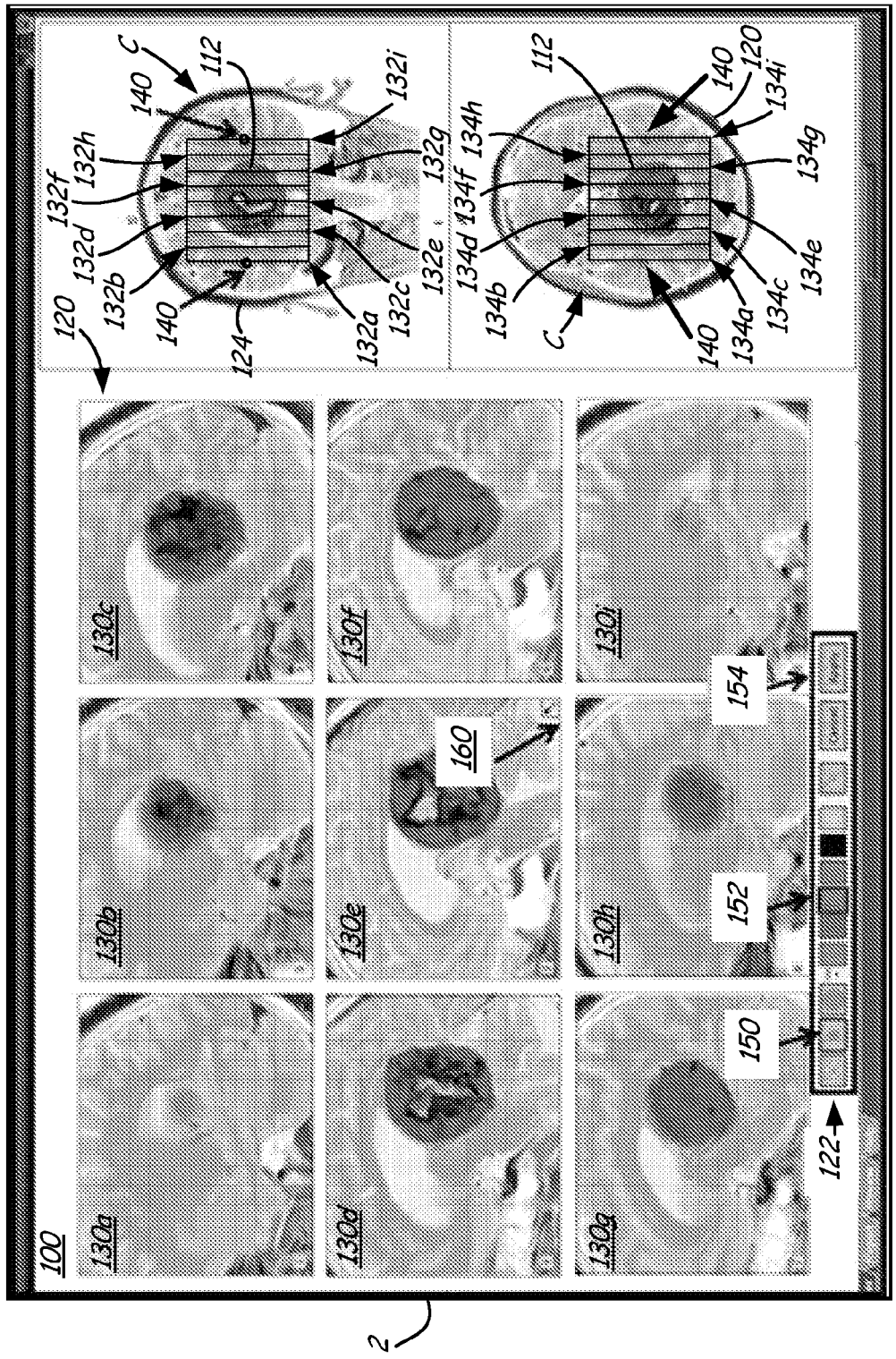
FIG. 9 is a screen shot of the user interface after a region of interest in the cranial image is selected showing a matrix of cross-sectional images and a cross section of the region of interest including reference indicia.

FIG. 9 is a screen shot of the user interface 100 after the user has defined the region of interest with the frame 110. The user interface 100 includes a matrix 120 of cross-sectional images, a toolbar 122, a coronal cross-sectional image 124 at the region of interest, and an axial cross-sectional image 126 the region of interest. The coronal cross-sectional image 124 and the axial cross-sectional image 126 are orthogonal to the cross-sectional images in the matrix 120. In the embodiment shown, the matrix 120 is a three-by-three matrix of images including cross-sectional images 130a, 130b, 130c, 130d, 130e, 130f, 130g, 130h, and 130i. The coronal cross-sectional image 124 includes a plurality of reference indicia (e.g., lines) 132a, 132b, 132c, 132d, 132e, 132f, 132g, 132h, and 132i), and the axial cross-sectional image 126 includes a plurality of reference indicia 134a, 134b, 134c, 134d, 134e, 134f, 134g, 134h, and 134i. The reference indicia 132a-i and 134a-i are substantially parallel with respect to each other and with respect to the frame 110 (FIG. 8) that defines the region of interest. The reference indicia 132a-i and 134a-i represent the locations of cut planes through the cranium C that provide the cross-sections shown in respective cross-sectional images. The cut planes are at different depths in the cranium C with respect to the frame 110.

While nine reference indicia 132, 134 and nine corresponding cross-sectional images 130 are shown, it will be appreciated that the user interface 100 may be adapted to provide any number of reference indicia 132, 134 for an equivalent number of cross-sectional images 130 in the matrix 120. For example, the user interface 100 may be configured to allow the user to increase or decrease the number reference indicia 132, 134 in the cross-sectional images 124, 126. This option may be provided to the user through a menu on the user interface 100, similar to menu 36 in FIG. 2, or through an option on toolbar 122.

The user interface 100 also includes a selector tool 140 provided on the cross-sectional views 124, 126. The selector tool 140 may be used to modify the distance between the reference indicia 132, 134 (individually or collectively), to modify the size of the volume of interest (i.e., to change the distance between reference indicia 132a, 134a and 132i, 134i), and/or to shift all reference indicia 132, 134 relative to the cranium C (not shown in FIG. 9) without affecting the spacing between the reference indicia 132, 134. The selector tool 140 may be constantly available for use on the cross-sectional views 124, 126, or it may be initiated through a menu similar to menu 36 described in FIG. 2 or through toolbar 122. When the selector tool 140 is used to modify the arrangement of the reference indicia 132, 134, the cross-sectional images 130a-i are correspondingly modified to represent images at the new locations of the reference indicia 132, 134. This allows the user to use the cross-sectional views 124 and 126 to focus the cross-sectional images 130a-i on the desired region or volume of interest the user wishes to edit, segment, and analyze.

The toolbar 122 includes various buttons and other interfaces that provide access to tools that may be used during segmentation and editing of the medical image being analyzed. In the embodiment shown in FIG. 9, the toolbar 122 includes region tool buttons 150 for initiating a region tool usable to define and modify one or more regions drawn around a portion of the cranium C. Actuation of the region tool buttons 150 may initiate or select the size of a paintbrush tool to guide or correct the region segmentation in the cross-sectional images 130a-130i. Toolbar 122 also includes segmentation selection buttons 152 to select a region or portion of the cranium C in the cross-sectional images 130a-130i. Each of the segmentation selection buttons 152 has a color that corresponds to the color of a part of the cranium C in the cross-sectional images 124, 126, and 130a-i. Thus, the segmentation selection buttons 152 can be used to isolate one element of the cranium C. Other embodiments of the toolbar may also include user controls to initiate or modify the contours of regions drawn in the cross-sectional images 130a-130i. The toolbar 122 further includes an "Apply" button 154 similar to "Apply" button 72 described above which allows the user to apply any contour edits to the cross-sectional images 130 and to interpolate the contours throughout the region of interest based on the edits. It will be appreciated that the toolbar 150 may include additional tools not specifically shown in the embodiment shown in FIG. 9. For example, the toolbar 122 may include a color overlay button to apply certain colors to certain parts of the cross-sectional images, an annotation tool to name and/or describe the various segmented region, or a measurement tool for determine dimensions of elements in the region of interest.

Figure 10:
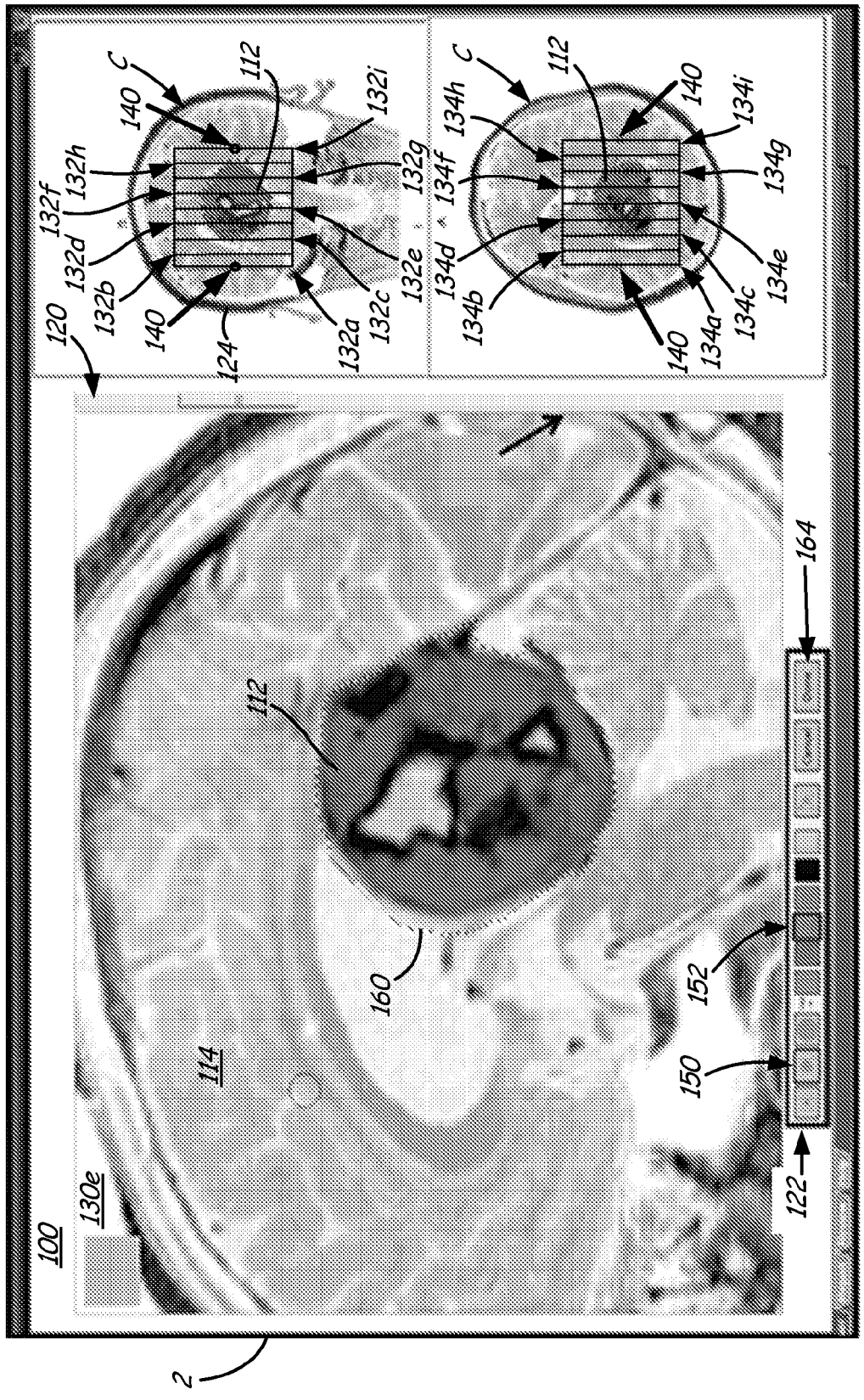
FIG. 10 is a screen shot of the user interface showing an enlarged cross-section from the matrix of cross-sectional cranial images for contour editing.

If a higher resolution is desired to edit the contours of a portion of the cranium C (e.g., the tumor 112), the user interface 100 allows the user to select and enlarge one of the cross-sectional views 130 in the matrix 120. In the embodiment shown in FIG. 9, the zoom tool 160 may be selected on cross-sectional image 130e to enlarge the image for contour or region editing. To illustrate, FIG. 10 is a screen shot of the user interface 100 after the zoom tool 160 is actuated, showing the cross-sectional view 130e from the matrix 120 in enlarged form. When enlarged, the outer contour 160 of the tumor 112 may be defined using the boundary tools 150 available on the toolbar 122. The enlarged view of cross-sectional view 130e provides a means for more intricate editing of the outer contour 160, allowing the user to precisely define the outer boundaries of the tumor 112. When the outer contour 160 has been modified, the "Done" button 164 may be actuated to apply the changes to the region of interest. A similar editing procedure may be used to define the outer contour 160 in the coronal cross-sectional image 124 and the axial cross-sectional image 126 to define the dimensions of the tumor 112 in all three dimensions. With the outer contour 160 defined in three dimensions, the precise size and shape of the tumor 112 can be determined.

It will be appreciated that while the user interface 10 and the user interface 100 have been described as separate embodiments, any of the features described in the user interface 10 may be implemented in the user interface 100, and vice versa. In addition, while the invention has been described with respect to the editing and segmentation of an aorta 14 and a cranium C, it will be appreciated that any portion of the anatomy that may be scanned and electronically assembled into a two- or three-dimensional image may also be provided for analysis on the user interface 10 or 100.

In summary, the present invention relates to a user interface for iterative segmentation and editing of a three dimensional medical image. The user interface is provided on a display and is responsive to user inputs in a medical imaging system. The user interface includes a framing tool for defining a region of interest on the medical image. An image matrix is then provided on the user interface, which includes a plurality of cross-sectional images each corresponding to a cross-section of the medical image at one of a plurality of cut planes within the region of interest. One or more reference views of the medical image are also displayed, which each include a plurality of reference indicia, each of which corresponds to a location of one of the plurality of cut planes. In some embodiments, a tool interface is also provided that includes a plurality of selectable control tools for use in segmenting and/or editing the cross-sectional images. The user interface of the present invention allows the user to focus the segmentation and editing process to a region of interest on the medical image, thereby reducing computation time. In addition, the boundaries of anatomical features are more precisely definable, since the user can modify the defined contours of an anatomical feature in any of the cross-sectional images of the image matrix. Furthermore, the size of the region of interest is changeable and the location of the cut planes are movable, thus allowing for precise segmentation and editing of the region of interest.

Various modifications and additions can be made to the exemplary embodiments discussed without departing from the scope of the present invention. While the embodiments described above refer to particular features, the scope of this invention also includes embodiments having different combinations of features and embodiments that do not include all of the above described features. For example, while the present invention has been described with regard to medical imaging and medical imaging systems, it will be appreciated that the user interface may be adapted for use in other types of three dimensional imaging systems.

What is claimed is:

1. A medical imaging system comprising:
a display;
a user input device; and
a processor associated with the display and user input device, the processor configured to provide a user interface for the display and editing of a three dimensional medical image on the display, the user interface responsive to user inputs on the user input device, the user interface comprising:
a framing tool operable to define a region of interest on the medical image;
an image matrix including a plurality of cross-sectional images each corresponding to a cross-section of the medical image at one of a plurality of cut planes within the region of interest;

one or more reference views of the medical image each including a plurality of reference indicia that each corresponds to a location of one of the plurality of cut planes; and a tool interface including a plurality of selectable control tools for use in segmenting and/or editing the cross-sectional images, the plurality of selectable control tools of the tool interface including a contouring/segmenting tool for defining contours and/or regions of an anatomical feature in the medical image, wherein the contouring/segmenting tool is usable in any of the cross-sectional images in the image matrix to define two-dimensional contours of the anatomical feature at each of the cut planes in the region of interest.

2. The medical imaging system of claim 1, wherein the image matrix is displayed after the region of interest is defined with the framing tool.

3. The medical imaging system of claim 1, wherein the one or more reference views are displayed concurrently with the image matrix.

4. The medical imaging system of claim 1, wherein the one or more reference views include a selector tool operable to move the plurality of reference indicia relative to the medical image, wherein movement of the plurality of reference indicia causes a corresponding change in location of the cross-sectional images.

5. The medical imaging system of claim 4, wherein the selector tool is further operable to modify dimensions of the region of interest.

6. The medical imaging system of claim 1, wherein the medical imaging system establishes a centerline of the anatomical feature based on the defined contours of the anatomical feature in the region of interest.

7. The medical imaging system of claim 6, wherein the cut planes are substantially perpendicular to the centerline.

8. The medical imaging system of claim 1, wherein the plurality of selectable control tools of the tool interface includes a measurement tool for measuring dimensions of the anatomical feature.

9. A medical imaging system comprising:
a display;
a user input device; and
a processor associated with the display and user input device, the processor configured to provide a user interface on the display for iterative segmentation and editing of a three dimensional medical image, the user interface responsive to user inputs on the user input device, the user interface comprising:

a first screen region displaying one or more two dimensional views of the medical image and a framing tool operable to define a region of interest on any of the one or more two dimensional views;

a second screen region displaying (a) an image matrix including a plurality of cross-sectional images each corresponding to a cross-section of the medical image at one of a plurality of cut planes within the region of interest, (b) one or more reference views of the medical image, each reference image including a plurality of reference indicia that each corresponds to a location of one of the plurality of cut planes, and (c) a tool interface including a plurality of selectable editing tools for use in modifying characteristics of the cross-sectional images, the plurality of selectable control tools includes a contouring/segmenting tool operable to define contours and/or regions of an anatomical feature in the medical image, wherein the contouring/segmenting tool is usable in any of the cross-sectional images in the image matrix to define two-dimensional contours of the anatomical feature at each of the cut planes in the region of interest.

10. The medical imaging system of claim 9, wherein the second screen is displayed after the region of interest is defined on the first screen.

11. The medical imaging system of claim 9, wherein the one or more reference views include a selector tool operable to move the plurality of reference indicia relative to the medical image, wherein movement of the plurality of reference indicia causes a corresponding change in location of the cut planes in the region of interest.

12. The medical imaging system of claim 11, wherein the selector tool is further operable to modify a size and/or location of the region of interest.

13. The medical imaging system of claim 9, wherein the medical imaging system establishes a centerline of the anatomical feature based on the defined contours of the anatomical feature in the region of interest.

14. The medical imaging system of claim 9, wherein the plurality of selectable control tools includes a measurement tool for measuring dimensions of the anatomical feature.

15. The medical imaging system of claim 9, wherein the cut planes are substantially parallel with respect to each other.

16. A method for providing a user interface for iterative segmentation and editing of a three dimensional medical image, wherein the user interface is provided on a display and is responsive to user inputs in a medical imaging system, the method comprising:

displaying the medical image on the display;

providing a framing tool for defining a region of interest on the medical image;

displaying an image matrix including a plurality of cross-sectional images when the region of interest is defined, each cross-sectional image corresponding to a cross-section of the medical image at one of a plurality of cut planes within the region of interest;

displaying one or more reference views of the medical image concurrently with the image matrix, wherein each of the one or more reference views includes a plurality of reference indicia that each corresponds to a location of one of the plurality of cut planes; and providing a contouring/segmenting tool for defining contours and/or regions of an anatomical feature in the medical image, the contouring/segmenting tool usable in any of the cross-sectional images in the image matrix to define two-dimensional contours of the anatomical feature at each of the cut planes in the region of interest.

17. The method of claim 16, and further comprising:

providing a selector tool on at least one of the one or more reference views, wherein the selector tool is operable to move the plurality of reference indicia relative to the medical image, wherein movement of the plurality of reference indicia causes a corresponding change in location of the cut planes in the region of interest.

18. The method of claim 17, wherein the selector tool is further operable to modify a size and/or location of the region of interest.

19. The method of claim 16, and further comprising:
displaying a centerline of the anatomical feature based on the defined contours of the anatomical feature in the region of interest.

20. The method of claim 16, and further comprising:
interpolating the contours of the anatomical feature between adjacent cut planes based on the contours defined using the contouring/segmenting tool.

21. The method of claim 20, and further comprising:
displaying the contours of the anatomical feature on the one or more reference views based on the defined and interpolated contours.

* * * * *